US011134775B2

(12) United States Patent
Weikert et al.

(10) Patent No.: US 11,134,775 B2
(45) Date of Patent: Oct. 5, 2021

(54) PEDAL ORGANIZER AND RELATED SYSTEM

(71) Applicants: Innovation Lab, LLC, Newport Beach, CA (US); Franciscan Missionaries of Our Lady Health System, Baton Rouge, LA (US)

(72) Inventors: Nicole Marie Weikert, Huntington Beach, CA (US); Matthew Ibarra, Lakewood, CA (US); Nikolai Poulsen, Irvine, CA (US); Moises Alberto Arriaga, Metairie, LA (US)

(73) Assignee: INNOVATION LAB, LLC, Newport Beach, CA (US)

( * ) Notice: Subject to any disclaimer, the term of this patent is extended or adjusted under 35 U.S.C. 154(b) by 0 days.

(21) Appl. No.: 16/272,939

(22) Filed: Feb. 11, 2019

(65) Prior Publication Data

US 2019/0246793 A1    Aug. 15, 2019

Related U.S. Application Data

(60) Provisional application No. 62/629,491, filed on Feb. 12, 2018.

(51) Int. Cl.
| *F16L 3/22* | (2006.01) |
| *A47B 21/06* | (2006.01) |
| *A61B 50/20* | (2016.01) |
| *F16L 3/223* | (2006.01) |
| *A61B 50/22* | (2016.01) |
| *A61B 17/00* | (2006.01) |
| *A47B 97/00* | (2006.01) |

(52) U.S. Cl.
CPC ............. *A47B 21/06* (2013.01); *A61B 50/20* (2016.02); *A61B 50/22* (2016.02); *F16L 3/223* (2013.01); *A47B 2097/003* (2013.01); *A61B 2017/00973* (2013.01)

(58) Field of Classification Search
CPC ......... A61B 50/20; A61B 50/22; A61B 17/00; A47B 81/00; A47B 21/06; F16L 3/223
See application file for complete search history.

(56) References Cited

U.S. PATENT DOCUMENTS

| 2,650,948 A | * | 9/1953 | Findlay ................. F16L 3/2235 |
| | | | 174/168 |
| 4,114,241 A | * | 9/1978 | Bisping ..................... F16B 2/22 |
| | | | 403/188 |
| 4,971,271 A | * | 11/1990 | Sularz ................. A61M 5/1418 |
| | | | 248/229.13 |

(Continued)

*Primary Examiner* — Kimberley S Wright
(74) *Attorney, Agent, or Firm* — Mintz Levin Cohn Ferris Glovsky and Popeo, P.C.

(57) ABSTRACT

One aspect of the disclosure relates to a pedal organizer. The pedal organizer may include: a first pedal retaining member including a front surface, a rear surface opposite the front surface, a top surface, and a bottom surface opposite the top surface; at least one aperture extending through the top surface to a depth within the first pedal retaining member, the at least one aperture extending from the front surface to the rear surface; and at least one void within the front surface of the first pedal retaining member, the at least one void being open to the at least one aperture without extending through to the rear surface, wherein portions of the front surface on opposing sides of the at least one void are substantially coplanar.

15 Claims, 14 Drawing Sheets

(56) References Cited

U.S. PATENT DOCUMENTS

| | | | | |
|---|---|---|---|---|
| 4,988,062 | A * | 1/1991 | London | A61G 7/0503 128/DIG. 26 |
| 6,227,502 | B1 * | 5/2001 | Derman | F16L 3/2235 248/68.1 |
| 6,345,873 | B1 * | 2/2002 | Kim | F16L 3/223 248/68.1 |
| 6,651,262 | B1 * | 11/2003 | Tinsley | A47K 13/10 4/246.1 |
| 6,702,129 | B1 * | 3/2004 | Harris | A47G 25/0664 211/172 |
| D488,054 | S * | 4/2004 | Myers | D8/356 |
| D587,102 | S * | 2/2009 | Morgan | D8/356 |
| 8,342,459 | B2 * | 1/2013 | Garrison | H01R 12/63 248/68.1 |
| 8,523,824 | B2 * | 9/2013 | Teirstein | A61M 25/02 604/174 |
| 8,998,151 | B2 * | 4/2015 | Hoek | H02G 3/32 248/68.1 |
| 10,300,248 | B2 * | 5/2019 | Taylor | A61M 25/02 |
| D853,336 | S * | 7/2019 | Barram | D13/155 |
| 2006/0089579 | A1 * | 4/2006 | Stivers | A61H 39/04 601/133 |
| 2010/0010475 | A1 * | 1/2010 | Teirstein | A61M 25/02 604/528 |
| 2011/0147542 | A1 * | 6/2011 | Hoek | F16L 3/223 248/68.1 |
| 2012/0216385 | A1 * | 8/2012 | Taylor | A61M 25/09 29/428 |
| 2016/0310203 | A1 * | 10/2016 | Gaspredes | A61B 18/1445 |

* cited by examiner

PEDAL ORGANIZER AND RELATED SYSTEM

CROSS-REFERENCE TO RELATED APPLICATIONS

This application claims priority to U.S. Patent Application Ser. No. 62/629,491 filed on Feb. 12, 2018, entitled "PEDAL ORGANIZER AND RELATED SYSTEM", the contents which is incorporated herein by reference in its entirety.

TECHNICAL FIELD

The present disclosure relates to a pedal organizer for foot pedals and related system.

BACKGROUND

Many operative tools are controlled by foot pedals. For example, in surgery, power drills, bipolar cautery devices, lasers, etc., may all be controlled by foot pedals. In some types of surgery, it may be necessary to use multiple tools thereby requiring multiple foot pedals for use thereof. Such surgeries may include microsurgery, microvascular surgery, neurology, ear, nose, or throat surgeries, laparoscopy, orthopedic, and/or endoscopy. During such surgeries, it may become difficult for the surgeon to locate and/or identify the foot pedal for the respective tool that they are using. In addition, foot pedals may slide or displace upon a force provided by the surgeon's foot during use.

SUMMARY

A first aspect of the disclosure relates to a pedal organizer. The pedal organizer may include: a first pedal retaining member including a front surface, a rear surface opposite the front surface, a top surface, and a bottom surface opposite the top surface; at least one aperture extending through the top surface to a depth within the first pedal retaining member, the at least one aperture extending from the front surface to the rear surface; and at least one void within the front surface of the first pedal retaining member, the at least one void being open to the at least one aperture without extending through to the rear surface, wherein portions of the front surface on opposing sides of the at least one void are substantially coplanar.

A second aspect of the disclosure relates to a pedal organizer system. The pedal organizer system may include: a pedal organizer including: a first pedal retaining member including a front surface, a rear surface opposite the front surface, a top surface, and a bottom surface opposite the top surface; at least one aperture extending through the top surface to a depth within the first pedal retaining member, the at least one aperture extending from the front surface to the rear surface; and at least one void within the front surface of the first pedal retaining member, the at least one void being open to the at least one aperture without extending through to the rear surface, wherein portions of the front surface on opposing sides of the at least one void is substantially coplanar; and a foot pedal having a rear surface contacting the front surface of the first pedal retaining member.

A third aspect of the disclosure relates to a pedal organizer. The pedal organizer may include: a base having at least one track thereon; and a pedal retaining member coupled to the base such that the pedal retaining member is configured to slide relative to the base about the at least one track.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

Figure 1:
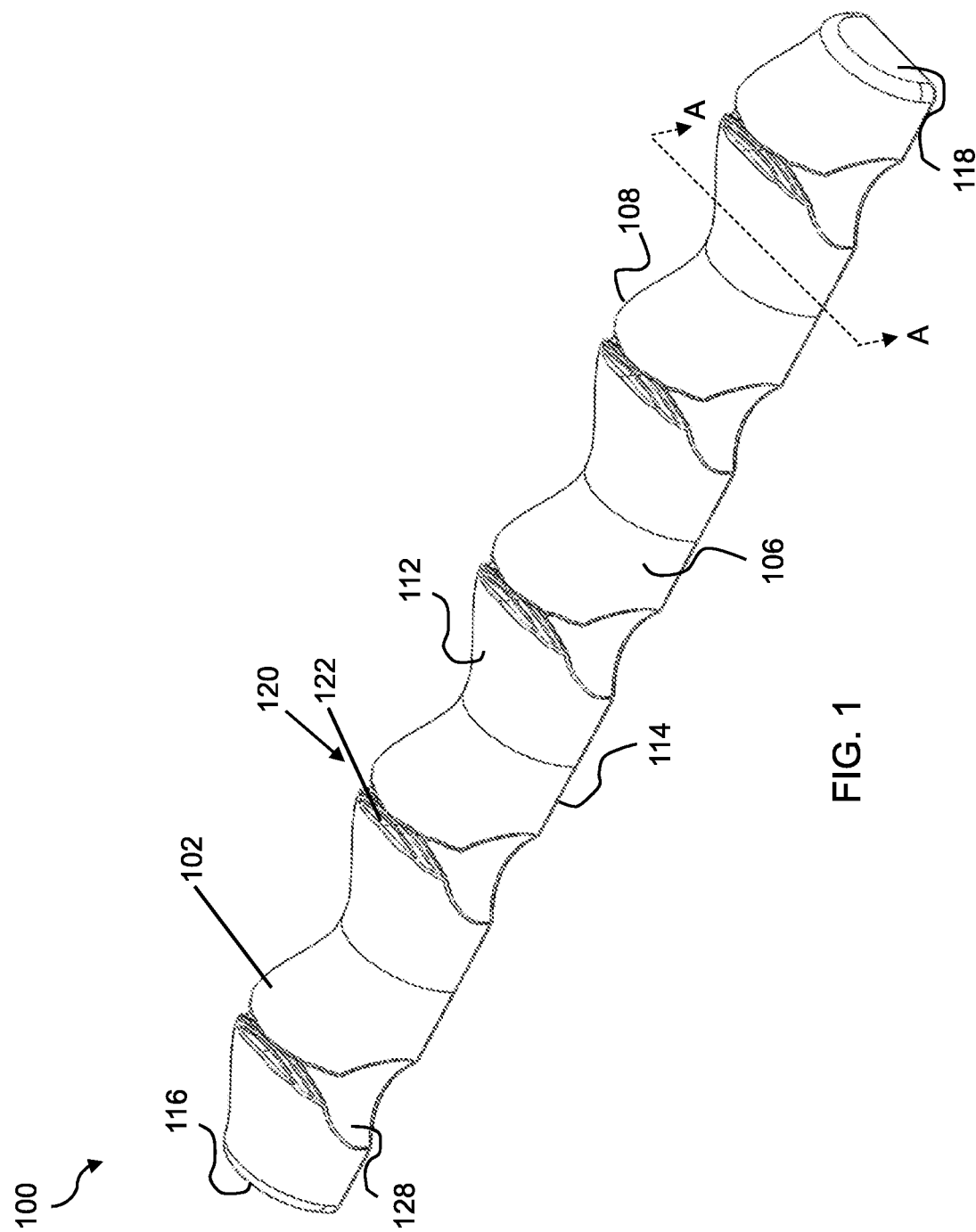
FIG. 1 shows a perspective view of a pedal organizer according to an embodiment of the disclosure.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION OF THE DRAWINGS

The present disclosure relates to a pedal organizer for foot pedals. The pedal organizer described herein includes a pedal retaining member that not only organizes the foot pedals, but also retains the foot pedals and prevents the foot pedals from sliding or moving during use. While the pedal organizer described herein is discussed relative to foot pedals for medical instruments, it is to be understood that the pedal organizer can be equally applicable to other fields wherein multiple foot pedals may be used and need to be organized or retained, e.g., dentistry, industrial machine shops, fabrication, manufacturing, sewing, music, etc.

Figure 2:
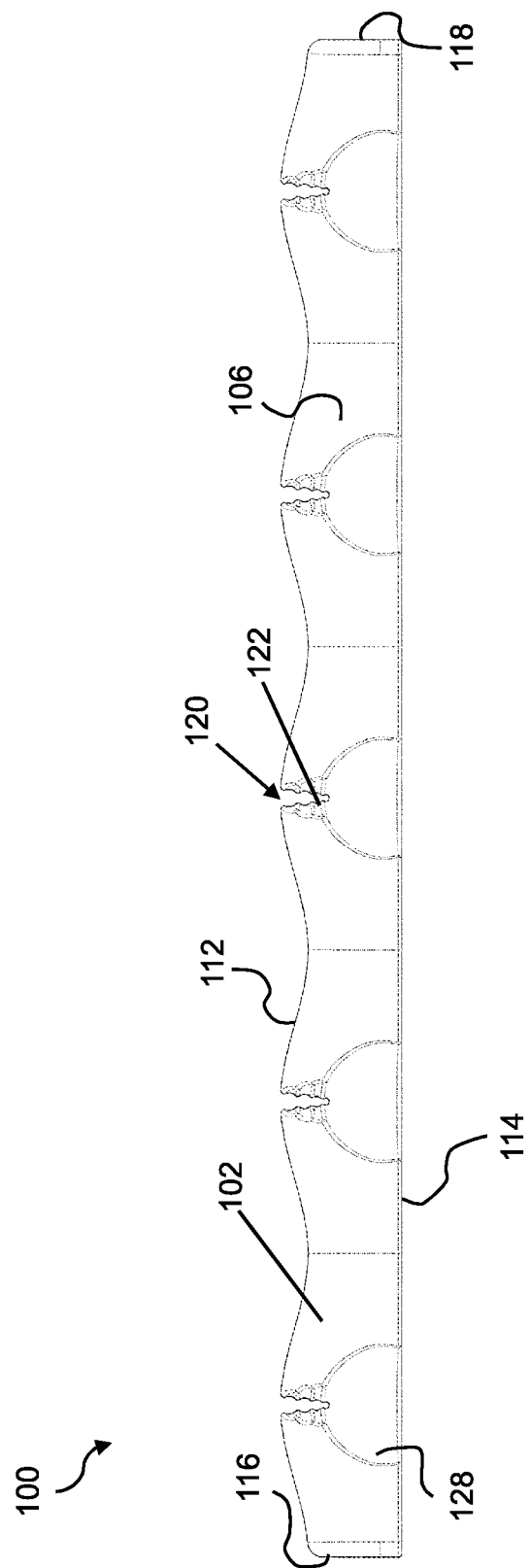
FIG. 2 shows a front-side view of a pedal organizer according to an embodiment of the disclosure.
Figure 3:
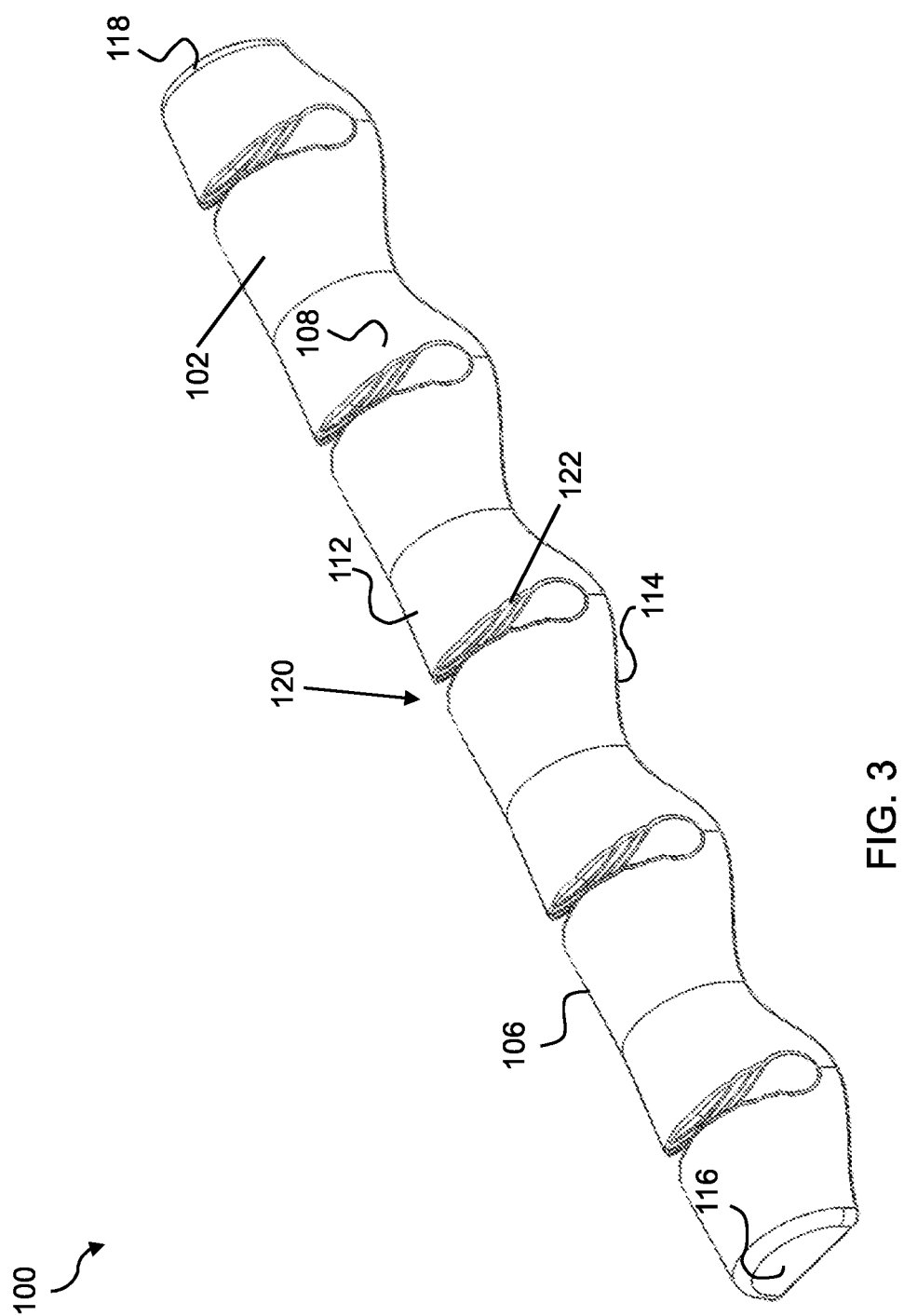
FIG. 3 shows a perspective view of a pedal organizer according to an embodiment of the disclosure.

Turning now to FIGS. 1-3, a pedal organizer 100 is shown according to an embodiment of the disclosure. Pedal organizer 100 may include a pedal retaining member 102 including a front surface 106 and a rear surface 108 opposite front surface 106. As used herein, front surface 106 may include a surface of pedal retaining member 102 that is or will be in direct contact with or facing the foot pedal that pedal retaining member 102 is to retain, and rear surface 108 may include a surface of pedal retaining member 102 that faces away from the foot pedal. Further, pedal retaining member 102 may include a top surface 112 and a bottom surface 114 opposite top surface 112. As used herein, bottom surface 114 may include a surface of pedal retaining member 102 that is or will be in direct contact with or that faces the ground/floor or other desired surface for which pedal retaining member 102 is placed (hereinafter "the floor"), and top surface 112 may include a surface of pedal retaining member 102 that faces away from the floor. Bottom surface 114 may be substantially planar for resting flatly or evenly on the floor. In some embodiments, at least one of top surface 112 or rear surface 114 of first pedal retaining member 102 may be substantially non-planar. Pedal retaining member 102 may also include a first end 116 and a second, opposing end 118. Each of first end 116 and second end 118 may be substantially planar or flat. As used herein, the terms "about," "substantially," "approximately," and variations thereof are intended to include the degree of error associated with measurement of the particular quantity based upon the equipment available at the time of filing the application.

Pedal organizer 100 may also include at least one aperture 120 extending through top surface 112 to a depth within pedal retaining member 102. Aperture 120 may extend from front surface 106 of pedal retaining member 102 to rear surface 108 of pedal retaining member. Aperture 120 may be sized and shaped to accommodate a cord or wire of a foot pedal therein. As shown, pedal organizer 100 may include five apertures 120. However, it is to be understood that any number of apertures 120 may be included without departing from aspects of the disclosure. Apertures 120 may be spaced apart within pedal retaining member 102 by a desired amount or distance in order to accommodate one or more foot pedals. In some embodiments (shown), aperture 120 may include a set of ribs 122 or may be ribbed. Set of ribs 122 may define channels of varying widths or diameters within aperture 120 to accommodate foot pedal wires/cords therein. Providing set of ribs 122 within aperture 120 allows for foot pedal wires/cords to snap into place within a given channel defined by set of ribs 122. In some embodiments, the widths or dimensions of the channels may decrease from top surface 112 through the depth of aperture 120 in order to accommodate and secure a variety of diameters for the wires/cords of the foot pedal as shown more clearly in FIG. 2. While only three ribs within each set of ribs 122 are shown, any number of ribs may be included without departing from aspects of the disclosure. In addition, it may be desirable to only provide some apertures 120 with set of ribs 122 while other apertures 120 may not include a set of ribs 122 at all.

In addition, pedal organizer 100 may also include at least one void 128 within the front surface 106 of pedal retaining member 102. Each void 128 may be open to at least one aperture 120 without extending through an entire width of pedal retaining member 102 to rear surface 108. Voids 128 may be sized and shaped to accommodate a wire connector positioned in the back side of a foot pedal. As shown, portions of front surface 106 on opposing sides of each void 128 may be substantially coplanar. This configuration allows a planar or flat surface for a foot pedal to rest or be pushed up against while providing a housing for a wire connector in the back of a foot pedal. Such a configuration may prevent kinking, turning, or twisting of the foot pedal relative to foot pedal retaining member 102. In addition, such a configuration may prevent damage to the wire and/or wire connector connection.

In some embodiments, pedal retaining member 102 may be composed of a tacky material, e.g., a tacky rubber material such as a silicone based rubber. In some embodiments, pedal retaining member 102 may be composed of any flexible or bendable material. In other embodiments, only bottom surface 114 may be composed of a tacky material, and the remainder of pedal retaining member 102 may be composed of some other material such as a rigid plastic or metal. In such an embodiment, set of ribs 122 may be composed of a tacky rubber material which may be adhered within apertures 120 to allow accommodating of wires/cords therein. In either embodiment (i.e., where pedal retaining member 102 and/or only bottom surface 114 are composed of tacky material), the tackiness of the material helps retain pedal retaining member 102 in a desired location on the floor or surface on which pedal retaining member 102 lies. That is, due to the tackiness of the material that makes up pedal retaining member 102 and/or bottom surface 114 of pedal retaining member 102, pedal retaining member may be prevented from sliding on the floor when a user applies pressure to a foot pedal that pedal retaining member 102 is retaining. In further embodiments, a separate tacky base may be adhered to a bottom surface of pedal retaining member 102.

Figure 4:
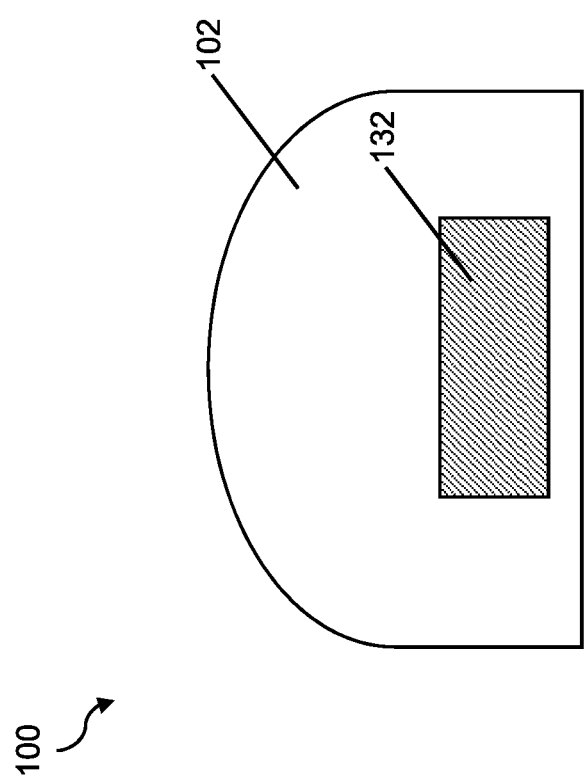
FIG. 4 shows a cross-sectional view of a pedal organizer according to an embodiment of the disclosure.

FIG. 4 shows a cross-sectional view of pedal organizer 100 taken along line A-A of FIG. 1. As shown in FIG. 4, a weighted bar 132 may be disposed within pedal retaining member 102. Weighted bar 132 may be of any desired weight or dimension to provide a desired additional weight to pedal retaining member 102. Further, weighted bar 132 may be of any desirable dimension, and may be positioned at any desirable position within pedal retaining member 102, such that weighted bar 132 does not interfere with apertures 120 (FIGS. 1-3) and/or voids 132 (FIGS. 1-3). Weighted bar 132 may include, for example, a metal bar, a wooden bar, a plastic bar, beads of metal, or sand. Weighted bar 132 may add additional weight to pedal retaining member 102 to aid in ensuring that pedal organizer 100 is of a weight sufficient enough to prevent a foot pedal from sliding during use by the user. More specifically, the combination of pedal retaining member 102 being composed of a tacky material (or having a bottom surface 112 being composed of a tacky material) as well as having a weighted bar 132 disposed therein, aids to ensure that pedal organizer 100 maintains its position during use of the foot pedals by a user. Said another way, when a user applies pressure to a foot pedal, the tackiness of pedal retaining member 102 and the added weight of weighted bar 132 may prevent foot pedals from sliding or displacing during use. In some embodiments, pedal organizer 100 may be manufactured by suspending weighted bar 132 inside a mold for pedal retaining member 102 and filling the mold with the material for pedal retaining member 102. In other embodiments, weighted bar 132 may be sandwiched between two or more parts of pedal retaining member 102 which may be coupled together.

Figure 5:
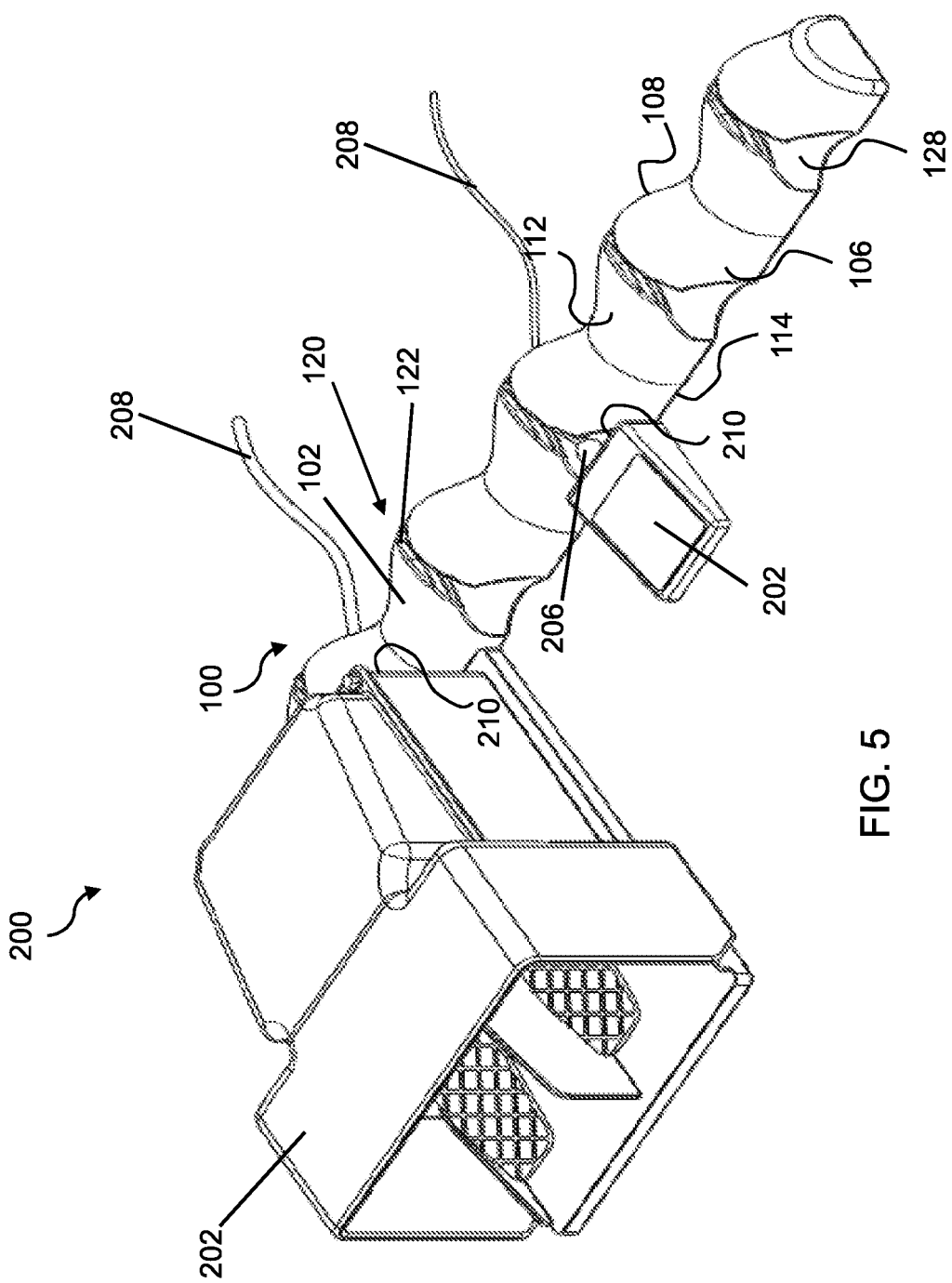
FIG. 5 shows a perspective view of a pedal organizer system according to an embodiment of the disclosure.

FIG. 5 shows a pedal organizer system 200 including pedal organizer 100 and one or more foot pedals 202. As shown, pedal organizer 100 is capable of being used with multiple foot pedals 202 of various sizes or dimensions. Foot pedals 202 may include foot pedals for surgical tools. However, it is to be understood that pedal organizer system 200 may also be used with other types of foot pedals or situations where one or more foot pedals may be used together, e.g., dentistry, industrial machine shops, fabrication, manufacturing, sewing, music, etc.

As shown in FIG. 5, foot pedal 202 may have a rear surface 208 contacting front surface 106 of first pedal retaining member 102. Foot pedal 202 may include a cable connector 206 (only one shown) connecting a cable 208 to rear surface 210 of foot pedal 202. When in use together with pedal retaining member 102, cable connector 206 may be substantially positioned within void 128 and cable 208 may be positioned within aperture 120. Positioning of cable connector 206 and cable 208 in this way enables foot pedal 202 to rest evenly/flatly against front surface 106 of pedal retaining member during use of foot pedal 202 and/or pedal organizer 100. Such positioning also prevents kinking of cable 206 and/or turning or twisting of cable 206 and/or foot pedal 202.

Figure 6:
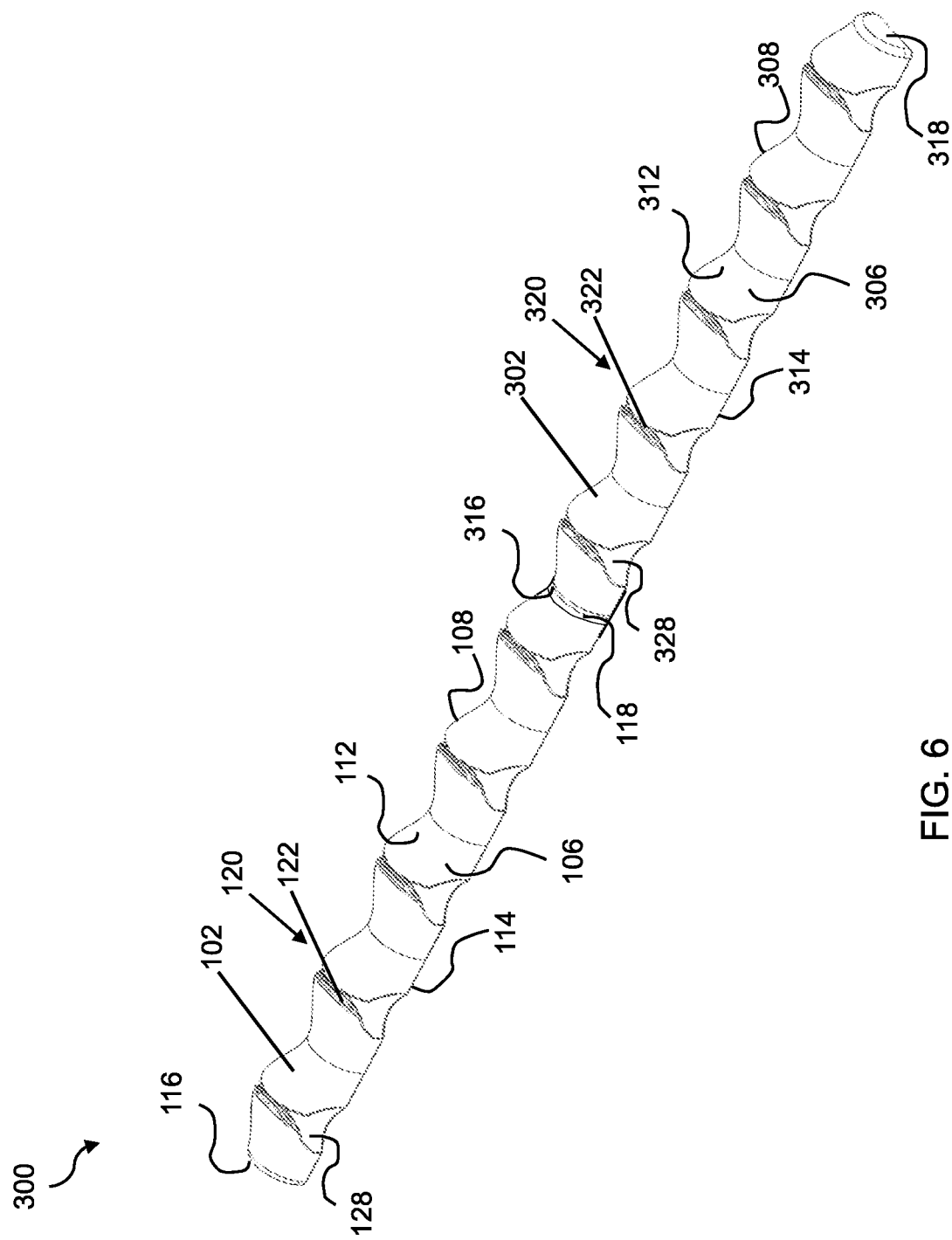
FIG. 6 shows a perspective view of a pedal organizer according to an embodiment of the disclosure.

It is to be understood that pedal retaining member 102 may be of any desired length without departing from aspects of the disclosure. However, in some embodiments, it may be desirable to provide more than one pedal retaining member for use together. FIG. 6 shows an example of a pedal organizer 300 including another pedal retaining member 302 positioned adjacent to pedal retaining member 102. Pedal retaining member 302 is positioned in contact with or adjacent to one of first end 116 or second end 118 of pedal retaining member 102. Like pedal retaining member 102, pedal retaining member 302 may include a front surface 306, a rear surface 308 opposing front surface 306, a top surface 312, a bottom surface 314 opposing top surface 312, a first end 316, and a second end 318. Further, pedal retaining member 302 may include voids 328 and apertures 320 optionally including set of ribs 322. In some embodiments, the configuration and spacing of voids 328 and apertures 320 may be identical to that of voids 128 and apertures 120 of pedal retaining member 102 such that pedal retaining member 102 and pedal retaining member 302 are substantially identical. In other embodiments, the configuration and spacing of voids 328 and apertures 320 may distinct from that of voids 128 and apertures 120 of pedal retaining member 102 such that pedal retaining member 102 and pedal retaining member 302 are not identical. Pedal retaining members 102, 302 may be of any desirable length or may be segmented without departing from aspects of the disclosure. Further, the ends (e.g., ends 116, 118, 316, 318) of each pedal retaining member may be shaped such that ends of adjacent pedal retaining members may matingly engage or fit together, for example, like puzzle pieces.

While not shown herein, in other embodiments, ends 116, 118, 316, 318 of pedal retaining members 102, 302 may matingly engage with one another. That is, instead of ends 116, 118, 316, 318 being substantially planar, ends 116, 118, 316, 318 may include tabs, projections, links, etc. for matingly engaging with an end of an adjacent pedal retaining member.

Figure 7:
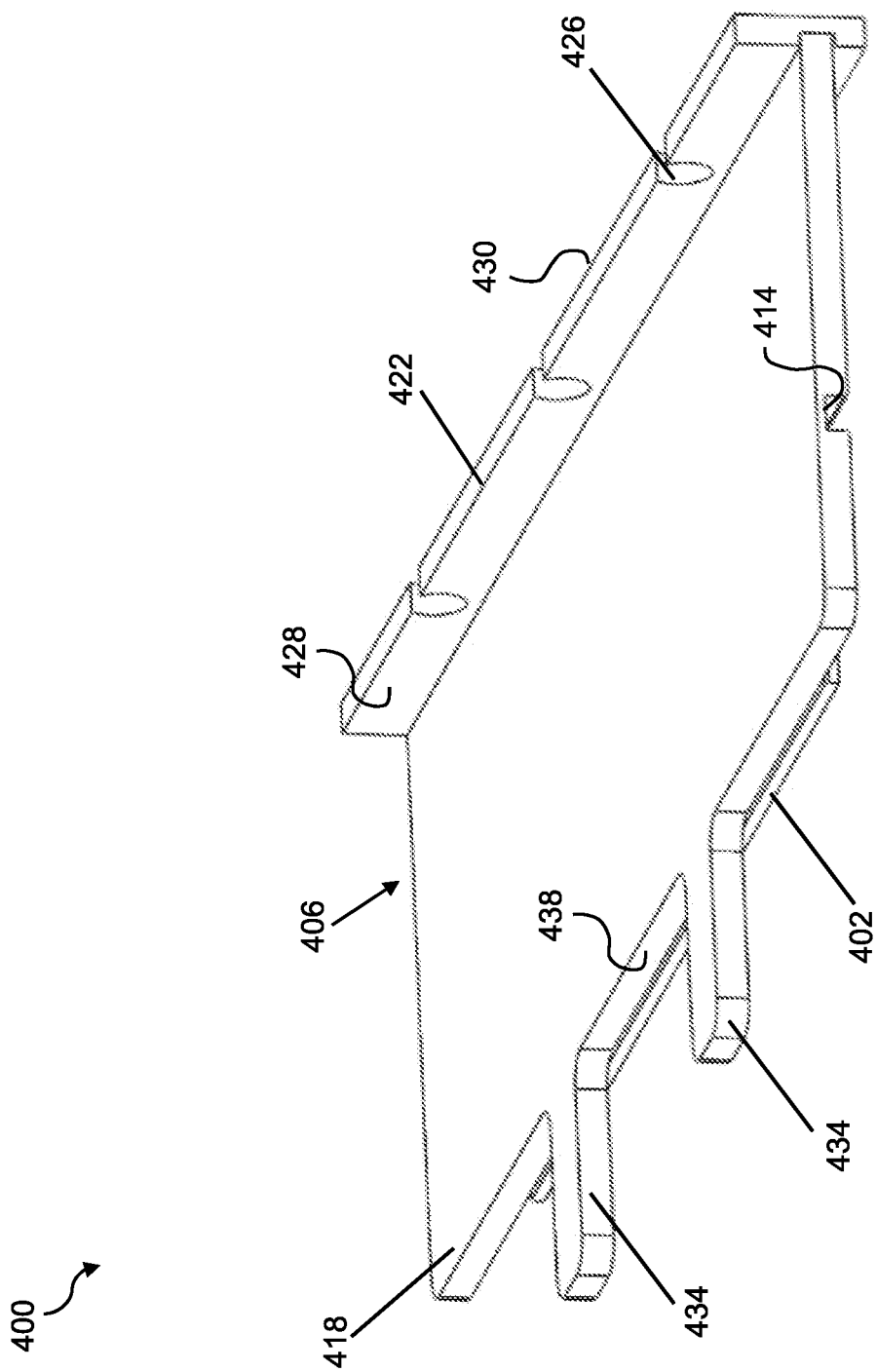
FIG. 7 shows a perspective view of a pedal organizer according to an embodiment of the disclosure.

Turning now to FIG. 7, a pedal organizer 400 according to another embodiment of the disclosure is shown. In this embodiment, pedal organizer 400 may include a base 402 and a pedal retaining member 406. Base 402 may have at least one track 410 thereon or therein. Base 402 may be substantially rectangular in shape and composed of a tacky material on the top and bottom surface. However, it is to be understood that base 402 may be of any other desirable shape without departing from the disclosure. In another embodiment, a separate tacky element may be adhered to the bottom surface of base 402.

Figure 8:
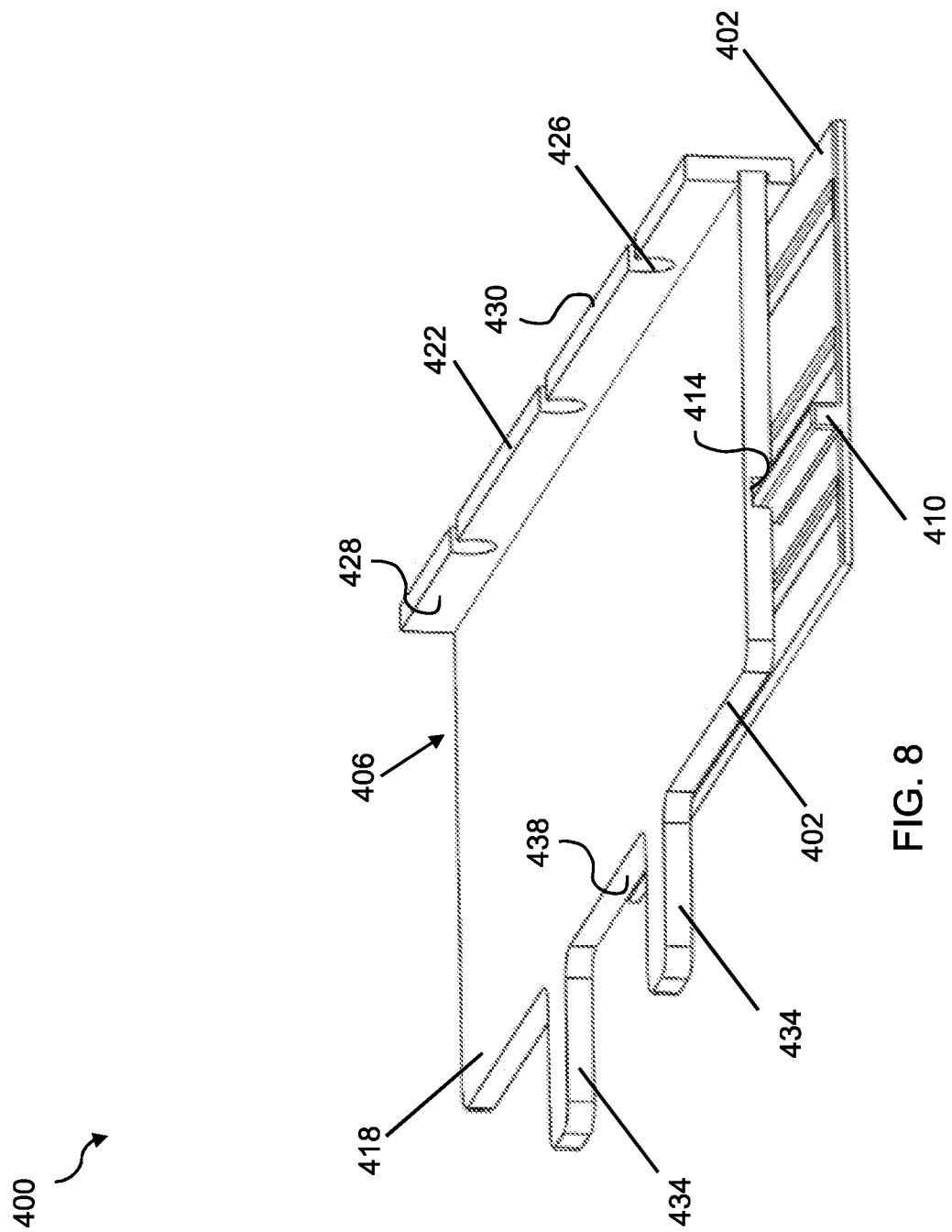
FIGS. 8-9 show perspective views of a pedal organizer according to an embodiment of the disclosure as a pedal retaining member is moved along a track of the base.
Figure 9:
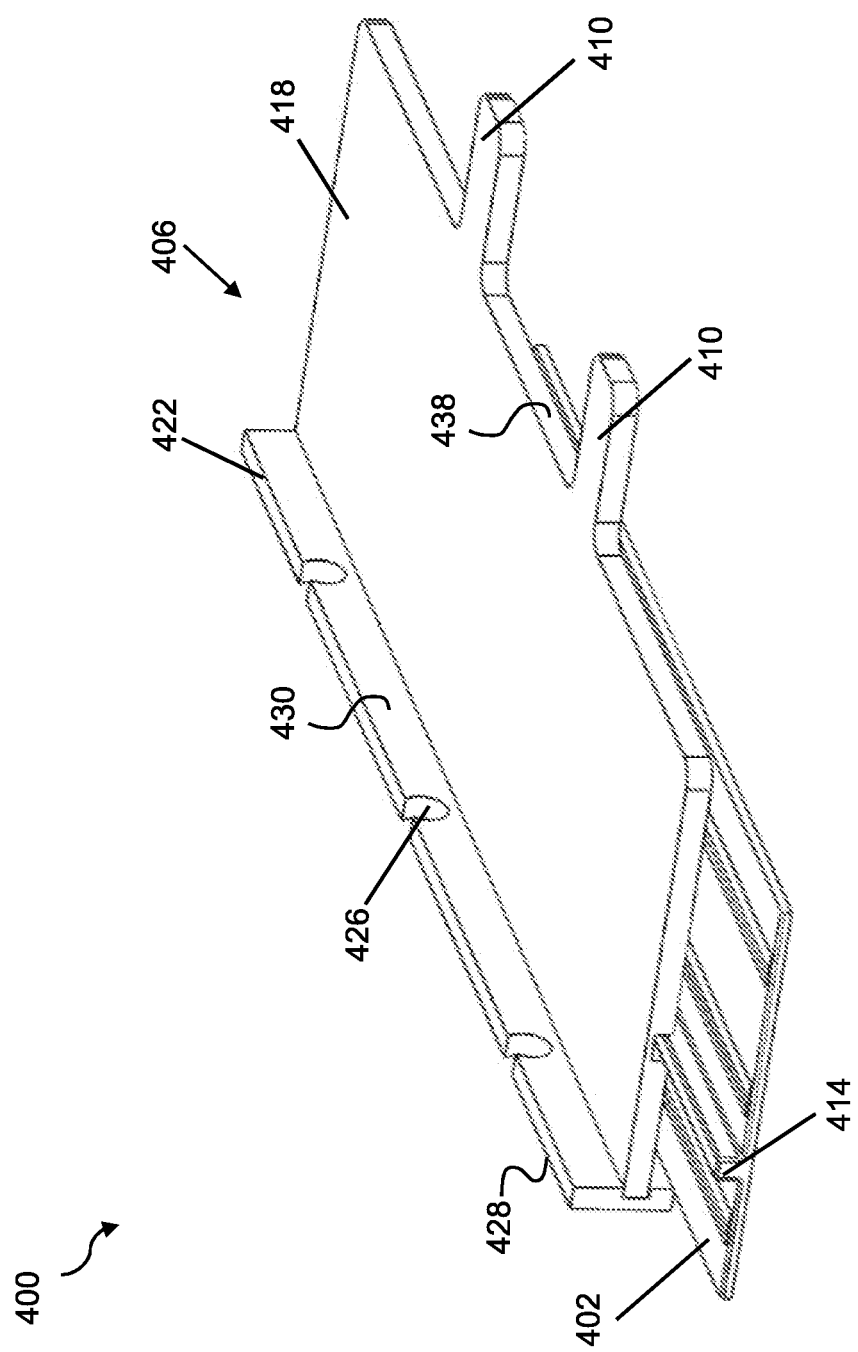
Figure 10:
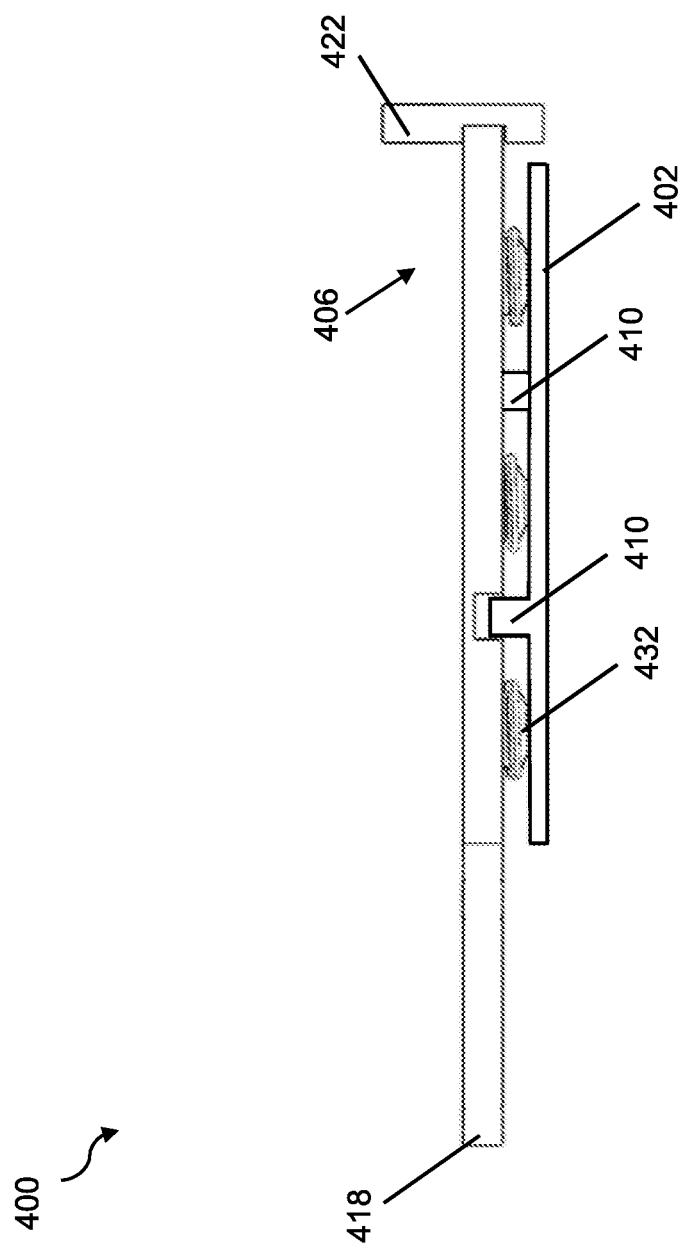
FIG. 10 shows a side view of a pedal organizer according to an embodiment of the disclosure.

As shown in FIGS. 8-10, base 402 may include two tracks 410. Pedal retaining member 406 may be coupled to base 402 such that pedal retaining member 406 is configured to slide relative to base 402 about tracks 410. More specifically, pedal retaining member 406 may include at least one slot 414 for matingly engaging with track 410 such that track 410 slides within the corresponding slot 414 during sliding of pedal retaining member 406. In other embodiments, it may be desirable for track 410 to be inverted such that track 410 is more like a slot disposed within base 402 while pedal retaining member 406 includes a projection (not shown) for matingly engaging with track 410. That is, in this embodiment, the projection may replace slot 414 to allow sliding of pedal retaining member 406 about track 410. In another example, track 410 and channel 414 configuration may be substantially T-shaped as shown in FIG. 10. In further embodiments, a magnetic coupling may be used along one or more tracks/slots for coupling of base 402 and pedal retaining member 406.

Pedal retaining member 406 may include a substantially planar surface 418 for resting one or more foot pedals, e.g., foot pedals 202 (FIG. 5), thereon. Further, pedal retaining member 406 may include a backboard member 422 extending substantially perpendicular to the substantially planar surface 418. Backboard member 422 may include at least one aperture 426 extending from a top surface of backboard member 422 to a depth within backboard member 422. Aperture 426 may also extend from a front surface 428 of backboard member 422 to a rear surface 430 of backboard member 422. Aperture 426 may be sized and shaped to accommodate wires/cords of foot pedals to be positioned on pedal retaining member 406. While not shown in FIG. 7, aperture 426 may include a set of ribs (e.g., set of ribs 122) like apertures 120 of FIG. 1 to provide channels of varying widths or diameters to accommodate wires/cords of foot pedals. Pedal retaining member 406 (including planar surface 418 and backboard member 422) may be composed of a substantially rigid material. For example, pedal retaining member 406 may be composed of a plastic or metal. In further embodiments, a tacky material may be painted on pedal retaining member 406 or adhered thereto. However, it is to be understood that pedal retaining member 406 may include any other rigid material capable of retaining foot pedals thereon and sliding relative to base 402.

Pedal retaining member 406 may also include at least one projection 434 extending from a front surface 438 of pedal retaining member 406. Front surface 438 of pedal retaining member 406 and projection 434 may be disposed on a surface that is opposite backboard member 422. Projection 434 may be configured to cause sliding of pedal retaining member 406 about base 402 e.g., via track 410 and slot 414, when actuated by a user (not shown). That is, a user may engage projection 434 with his or her foot to apply a slight force to projection 434 to slide pedal retaining member 406 about base 402 in a desired direction in order to obtain or access a desired foot pedal positioned on pedal retaining member 406 (see FIGS. 8-9). This allows the user to access the foot pedals on pedal retaining member 406 while remaining in a relatively stationary position. For example, in surgery, a doctor may remain in the same position relative to the patient they are working on, and merely move their foot to slide pedal retaining member 406 about track 410 to access the desired foot pedal positioned thereon. In other embodiments, however, projection 434 may not be necessary and the user can engage the top surface of pedal retaining member 402 with his or her foot to slide pedal retaining member 406 about base 402.

Figure 11:
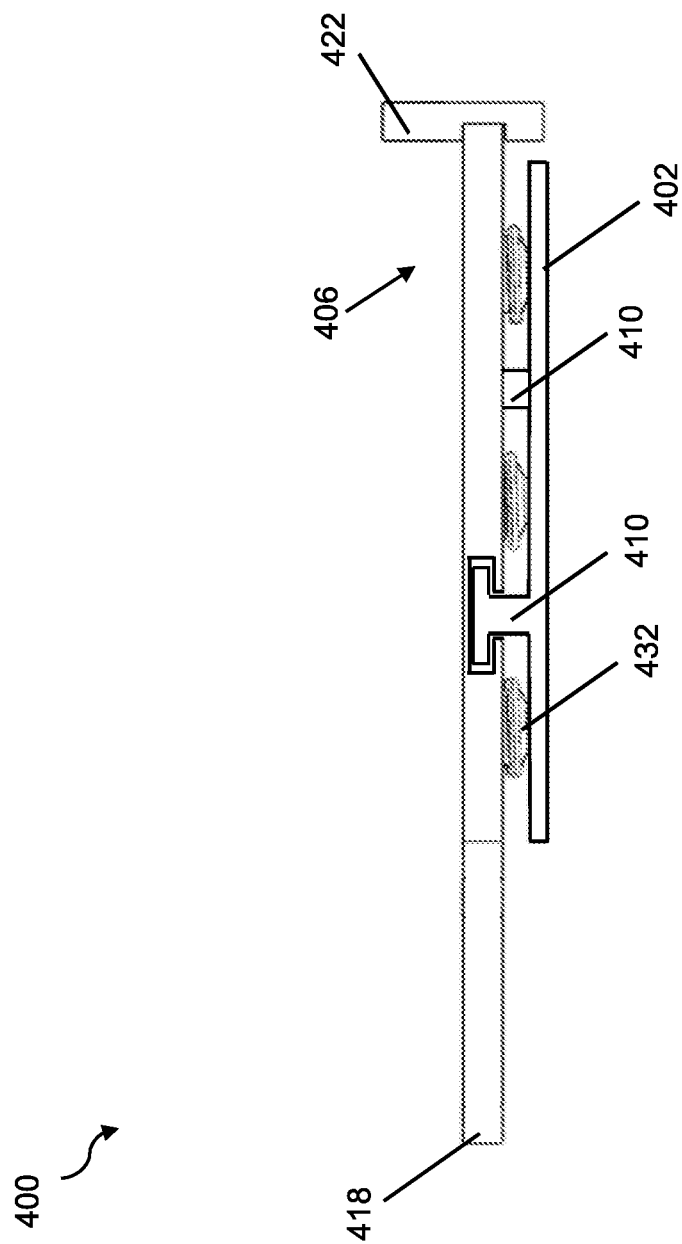
FIG. 11 shows a side view of a pedal organizer according to an embodiment of the disclosure.

Turning to FIGS. 10-11, pedal organizer 400 may include optional roller bearings or spacers (hereinafter "spacers") 432 disposed between base 402 and pedal retaining member 406. Spacers 432 may assist in the sliding of pedal retaining member 406 relative to base 402. In some embodiments, spacers 432 may not be necessary at all. For example, if the surfaces of pedal retaining member 406 and base 402 which face each other have a low coefficient of friction, no spacers 432 may be needed. In further embodiments, other means for enabling smooth sliding of pedal retaining member 406 relative to base 402 may be used. For example, a channel (not shown) may be formed within the surfaces of base 402 and pedal retaining member 402 that face each other. Such channels may be sized and shaped for accommodating a ball or rod (not shown) which may assist sliding of pedal retaining member 406 relative to base 402.

Figure 12:
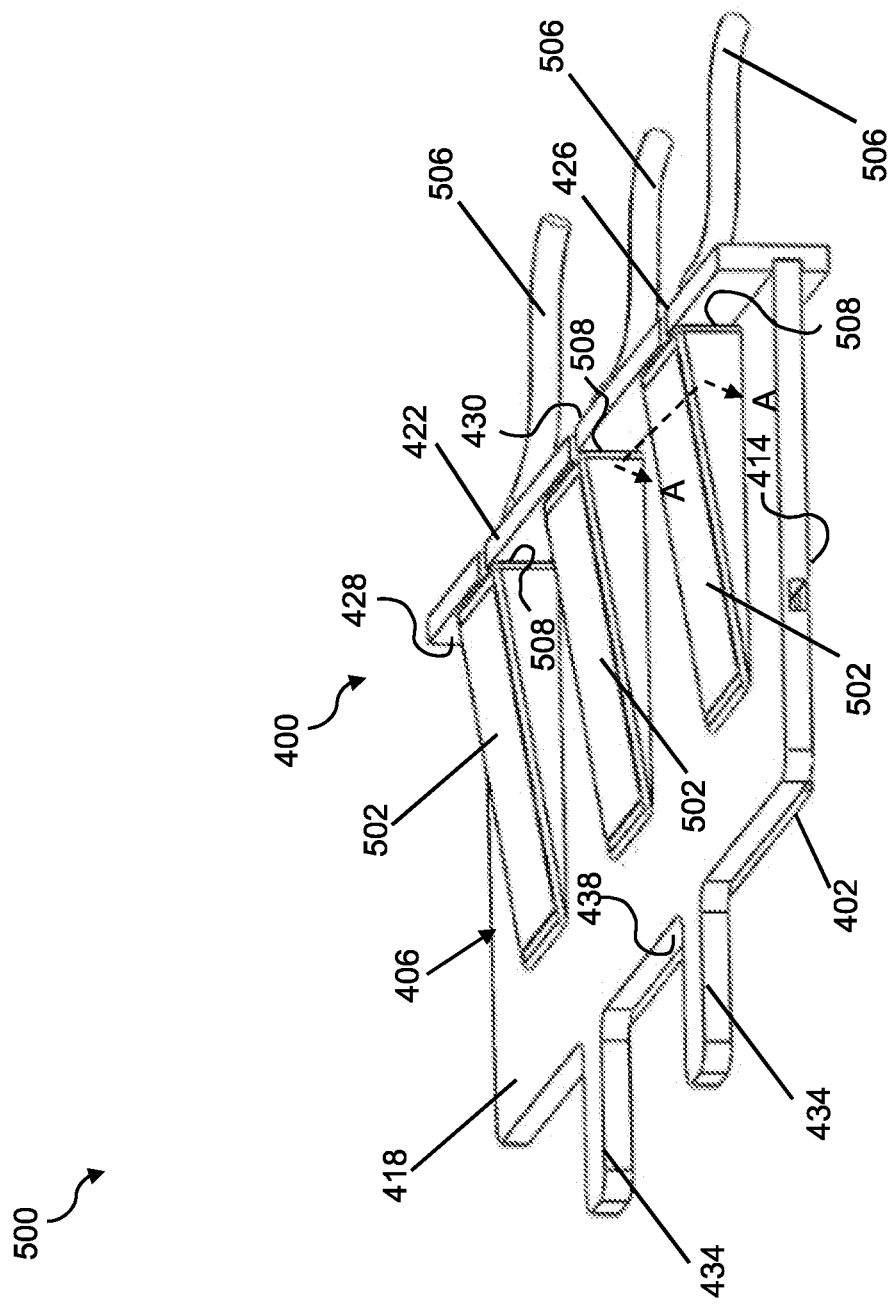
FIG. 12 shows a perspective view of a pedal organizer system according to an embodiment of the disclosure.

FIG. 12 shows a pedal organizer system 500 including pedal organizer 400 and one or more foot pedals 502. As shown, pedal organizer 400 is capable of being used with multiple foot pedals 402 of various sizes or dimensions. Foot pedals 402 may include foot pedals for surgical tools. However, it is to be understood that pedal organizer system 500 may also be used with other types of foot pedals or situations where one or more foot pedals may be used together, e.g., dentistry, industrial machine shops, fabrication, manufacturing, sewing, music, etc.

As shown in FIG. 12, foot pedal 502 may have a rear surface 508 contacting front surface 442 of backboard member 422 of pedal retaining member 402. Foot pedal 502 may include a cable connector (not shown in FIG. 12, but similar to cable connector 206 of FIG. 6) connecting a cable 506 to rear surface 508 of foot pedal 502. In this embodiment, the cable connector may fit within aperture 426. However, in other embodiments a void (not shown in FIG. 12, but similar to void 128 of FIGS. 1 and 6) may be formed within backboard member 422 for accommodating the cable connector therein.

Figure 13:
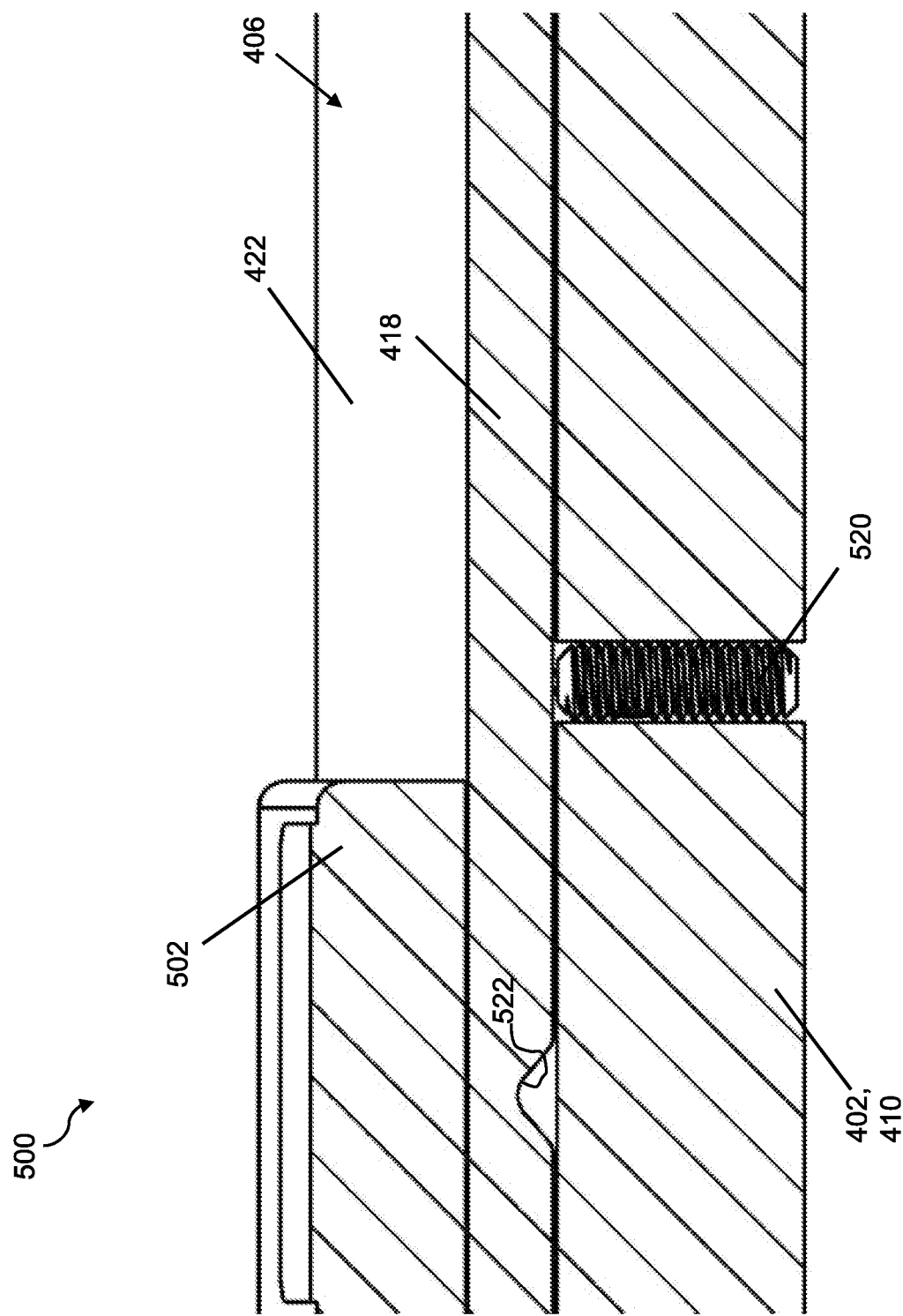
FIGS. 13-14 show a cross-sectional view of an embodiment of a pedal organizer system taken along line A-A of FIG. 12.
Figure 14:
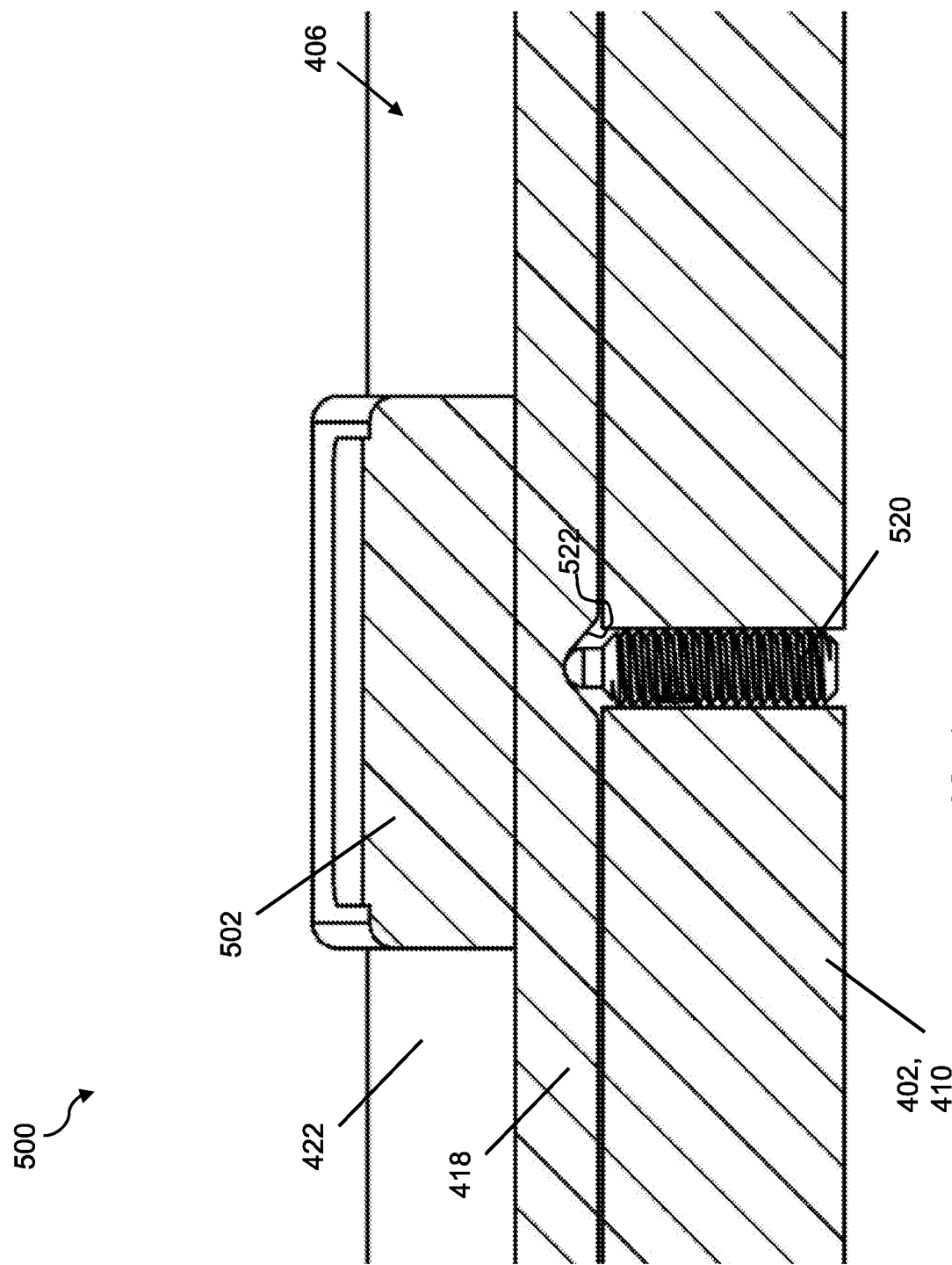

FIGS. 13-14 show a cross section of pedal organizer system 500 taken along line A-A of FIG. 12 along a track 410 according to another embodiment of the disclosure. In this embodiment, pedal organizer system 500 further includes an indexing mechanism. More specifically, one or more locking means 520 may be provided within base 402. Locking means 520 may include, for example, a spring plunger, a pin, a tab, an arm, or a rod, positioned within a hole or channel formed within base 406. However, locking means 520 may include any other means for providing a mechanism for indexing. Complementary voids 522 may be formed within a surface of pedal retaining member 406 that faces base 406. Voids 522 may be positioned within pedal retaining member 406 at a position of about beneath each foot pedal 502. Locking means 520 and voids 522 together may enable the user to identify which foot pedal is in front of them by the locking and unlocking of locking means 520. FIG. 13 shows locking means 520 in a disengaged position, when locking means 520 is not partially disposed within void 522 in an unlocked position. FIG. 14 shows locking means 520 in an engaged position, when locking means 520 is partially disposed within void 520 in a locked position.

During use, the user may slide pedal retaining member 406 relative to base as discussed elsewhere herein. However, during the sliding, pedal retaining member 406 may slide such that locking means 520 locks and unlocks or engages and disengages between adjacent apertures 522 beneath adjacent foot pedals 502 on pedal retaining member 406. This allows the user to identify which foot pedal 502 is in front of him or her by feeling the clicking/indexing or engaging/disengaging of locking means 520.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The particular embodiments disclosed above are illustrative only, as the disclosure may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the disclosure. Note that the use of terms, such as "first," "second," "third" or "fourth" to describe various processes or structures in this specification and in the attached claims is only used as a shorthand reference to such steps/structures and does not necessarily imply that such steps/structures are performed/formed in that ordered sequence. Of course, depending upon the exact claim language, an ordered sequence of such processes may or may not be required. Accordingly, the protection sought herein is as set forth in the claims below.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A pedal organizer comprising:
    a first pedal retaining member including a front surface, a rear surface opposite the front surface, a top surface, and a bottom surface opposite the top surface;
    at least one aperture extending through the top surface to a depth within the first pedal retaining member, the at least one aperture extending from the front surface to the rear surface, each aperture of the at least one aperture including a set of ribs defining a channel;
    at least one void extending into the front surface of the first pedal retaining member and shaped to receive a wire connector of a foot pedal, each of the at least one void being open to a respective aperture of the at least one aperture without extending through to the rear surface thereby allowing a wire extending from the wire connector to secure within the channel of the respective aperture, wherein portions of the front surface on opposing sides of each void are substantially coplanar to allow the foot pedal to mate thereagainst; and a weighted bar positioned within the first pedal retaining member and extending below and adjacent the at least one aperture to prevent movement of the first pedal retaining member.

2. The pedal organizer of claim 1, wherein the bottom surface of the first pedal retaining member is composed of a tacky material.

3. The pedal organizer of claim 1, wherein the first pedal retaining member is composed of a tacky material.

4. The pedal organizer of claim 1, wherein the weighted bar includes at least one of: a metal bar, a wooden bar, a plastic bar, beads of metal, or sand.

5. The pedal organizer of claim 4, wherein the width of the channel decrease from the top surface through the depth of the at least one aperture.

6. The pedal organizer of claim 1, wherein the first pedal retaining member further includes: a first end and second end, each end being substantially planar.

7. The pedal organizer of claim 6, further comprising:
a second pedal retaining member positioned proximate to the first pedal retaining member.

8. The pedal organizer of claim 7, wherein the second pedal retaining member is positioned in contact with one of the first end or the second end of the first pedal retaining member.

9. The pedal organizer of claim 1, wherein at least one of the top surface or the rear surface of the first pedal retaining member is substantially non-planar.

10. The pedal organizer system comprising:
a pedal organizer including:
a first pedal retaining member including a front surface, a rear surface opposite the front surface, a top surface, and a bottom surface opposite the top surface;
at least one aperture extending through the top surface to a depth within the first pedal retaining member, the at least one aperture extending from the front surface to the rear surface, each aperture of the at least one aperture including a set of ribs defining a channel;
at least one void extending into the front surface of the first pedal retaining member and shaped to receive a part of the foot pedal, each of the at least one void being open to a respective aperture of the at least one aperture without extending through to the rear surface thereby allowing a cable extending from the foot pedal to secure within the channel of the respective aperture, wherein portions of the front surface on opposing sides of each void is substantially coplanar; and
a weighted bar positioned within the first pedal retaining member and extending below and adjacent the at least one aperture to prevent movement of the first pedal retaining member.

11. The pedal organizer system of claim 10, further comprising:
a cable connector connecting the cable to the rear surface of the foot pedal, the cable connector being substantially positioned within the void and the cable being positioned within the at least one aperture.

12. The pedal organizer system of claim 10, the bottom surface of the first pedal retaining member is composed of a tacky material such that the foot pedal is prevented from being displaced when in use.

13. The pedal organizer system of claim 10, wherein the width of the channel decreases from the top surface through the depth of the at least one aperture.

14. The pedal organizer system of claim 10, wherein the first pedal retaining member further includes: a first end and second end, each end being substantially planar.

15. The pedal organizer system of claim 14, wherein a second pedal retaining member is positioned in contact with one of the first end or the second end of the first pedal retaining member.

* * * * *